US010000819B2

(12) United States Patent
Demarco et al.

(10) Patent No.: US 10,000,819 B2
(45) Date of Patent: Jun. 19, 2018

(54) SEQUENCES AND THEIR USE FOR DETECTION AND CHARACTERIZATION OF E. COLI O157:H7

(71) Applicant: E. I. DU PONT DE NEMOURS AND COMPANY, Wilmington, DE (US)

(72) Inventors: Daniel R. Demarco, Wilmington, DE (US); Mark A. Jensen, West Chester, PA (US); Stephen Varkey, Newark, DE (US)

(73) Assignee: Qualicon Diagnostics LLC, Wilmington, DE (US)

( * ) Notice: Subject to any disclaimer, the term of this patent is extended or adjusted under 35 U.S.C. 154(b) by 212 days.

(21) Appl. No.: 14/769,493

(22) PCT Filed: Feb. 18, 2014

(86) PCT No.: PCT/US2014/016797
§ 371 (c)(1),
(2) Date: Aug. 21, 2015

(87) PCT Pub. No.: WO2014/130416
PCT Pub. Date: Aug. 28, 2014

(65) Prior Publication Data
US 2015/0376686 A1 Dec. 31, 2015

Related U.S. Application Data

(60) Provisional application No. 61/767,458, filed on Feb. 21, 2013.

(51) Int. Cl.
*C12Q 1/68* (2006.01)
(52) U.S. Cl.
CPC ....... *C12Q 1/689* (2013.01); *C12Q 2600/158* (2013.01)
(58) Field of Classification Search
None
See application file for complete search history.

(56) References Cited

U.S. PATENT DOCUMENTS

| | | | |
|---|---|---|---|
| 4,678,812 | A | 7/1987 | Bollin, Jr. et al. |
| 4,683,195 | A | 7/1987 | Mullis et al. |
| 4,683,202 | A | 7/1987 | Mullis |
| 4,762,857 | A | 8/1988 | Bollin, Jr. et al. |
| 5,210,015 | A | 5/1993 | Gelfand et al. |
| 5,487,972 | A | 1/1996 | Gelfand et al. |
| 5,538,848 | A | 7/1996 | Livak et al. |
| 5,804,375 | A | 9/1998 | Gelfand et al. |
| 5,994,056 | A | 11/1999 | Higuchi |
| 6,171,785 | B1 | 1/2001 | Higuchi |
| 6,312,930 | B1 | 11/2001 | Tice, Jr. et al. |
| 6,326,145 | B1 | 12/2001 | Whitcombe et al. |
| 6,365,723 | B1 | 4/2002 | Blattner et al. |
| 2006/0051769 | A1 | 3/2006 | Barts |
| 2011/0020823 | A1 | 1/2011 | Burns |
| 2011/0165568 | A1 | 7/2011 | Vatta et al. |
| 2012/0309003 | A1 | 12/2012 | Cummings et al. |

FOREIGN PATENT DOCUMENTS

| | | |
|---|---|---|
| WO | 9711197 A1 | 3/1997 |
| WO | 0236827 A1 | 5/2002 |
| WO | 2007097410 A1 | 8/2007 |

OTHER PUBLICATIONS

International Search Report for International Application No. PCT/US2014/016797, filed Feb. 18, 2014.
"*Escherichia coli* O157:H7 genomic sequence comprising 0-islands", Aug. 30, 2002, XP002723661.
"Sequence 96 from U.S. Pat. No. 6,365,723", Jun. 21, 2002, XP002723662.
"*E. coil* 055:H7 detection/identification related contig DNA, SEQ ID 429", Aug. 18, 2011, XP002723659.
"*E coli* 055:H7 detection/identification related contig DNA, SEQ ID 522", Aug. 18, 2011, XP002723660.
"*E coli* 055:H7 detection/identification related contig DNA, SEQ ID 970", Aug. 18, 2011, XP002723697.
"*Escherichia coil* 0104:H4 genomic DNA, SEQ:300", Jan. 31, 2013, XP002723656.
"*Escherichia coli* HUSEC41 genomic DNA, SEQ:672", Jan. 31, 2013, XP002723657.
"*Escherichia coli* HUSEC41 genomic DNA, SEQ:921", Jan. 31, 2013, XP002723658.
"*Escherichia coli* HUSEC41 genomic DNA, SEQ:546", Jan. 31, 2013, XP002723698.
"*Escherichia coli* nucleic acid probe SEQ ID No. 128821", Nov. 15, 2007, XP002723663.
"*Escherichia coli* nucleic acid probe SEQ ID No. 128810", Nov. 15, 2007, XP002723664.
"*Escherichia coli* nucleic acid probe SEQ ID No. 128816", Nov. 15, 2007, XP002723665.
"*Escherichia coli* nucleic acid probe SEQ ID No. 128808", Nov. 15, 2007, XP002723666.
"*Escherichia coli* nucleic acid probe SEQ ID No. 128819", Nov. 15, 2007, XP002723667.
Andrews et al., "Food Sample and Preparation of Sample Homogenate", Chapter 1 in Bacteriological Analytical Manual, 8th Edition, Revision A, Association of Official Analytical Chemists, Arlington, VA, 1984.
Ausubel, F. M. et al., Current Protocols in Molecular Biology, vol. 1, published by Greene Publishing Assoc. and Wiley-Interscience (1987).

(Continued)

*Primary Examiner* — Samuel C Woolwine
(74) *Attorney, Agent, or Firm* — Potter Anderson and Corroon LLP

(57) ABSTRACT

This invention relates to a rapid method for detection and characterization of *Escherichia coli* bacteria serotype O157:H7 based on the presence of nucleic acid sequences, in particular, to a PCR-based method for detection, and to oligonucleotide molecules and reagents and kits useful therefore. This method is preferably employed to detect *E. coli* O157:H7 in a food or water sample, such as a beef enrichment. The present invention further relates to replication compositions and kits for carrying out the method of the present invention.

15 Claims, No Drawings

(56) References Cited

OTHER PUBLICATIONS

Basu et al., "Effect of site-specifically located mitomycin C-DNA monoadducts on in vitro DNA synthesis by DNA polymerases", Biochemistry 32, 4708-4718.

Carrino et al., "Nucleic acid amplification methods", Journal of Microbiological Methods 23 (1995) 3-20.

Carters et al., "Design and use of scorpions fluorescent signaling molecules", Methods in Molecular Biology, Humana Press Inc. NJ, US, vol. 429, 2008, pp. 99-115.

Fahy et al., "Self-sustained SequenceReplication (3SR): An Isothermal Transcription based Amplification System Alternative to PCR", PCR Methods and Applications, Cold Spring Harbor Laboratory: Cold Spring Harbor, NY (1991), pp. 25-33).

Kawasaki, "Amplification Of RNA", PCR Protocols: A Guide to Methods and Applications, M. A. Innis et al., Eds., Academic Press (1990), pp. 21-27.

Pfeffer et al., "Applications of DNA Amplification Techniques in Veterinary Diagnostics", Veterinary Research communications, 19 (1995) 375-407.

Ross, et al., "Discrimination within Phenotypically Closely Related Definitive Types of *Salmonella enterica* Serovar Typhimurium by the Multiple Amplification of Phage Locus Typing Technique", Journal of Clinical Microbiology, 2005, vol. 43, No. 4, 2005, American Society for Microbiology.

Sambrook, J., Fritsch, E. F. and Maniatis, T., Molecular Cloning: A Laboratory Manual, 2nd ed., Cold Spring Harbor Laboratory: Cold Spring Harbor, NY (1989).

Sharma et al., "Real-time reverse transcription-multiplex PCR for simultaneous and specific detection of rfbE and eae genes of *Escherichia coli* 0157:H7", Molecular and Cellular Probes, Academic Press, London, GB, vol. 20, No. 5, 2006.

Tabor et al., "A bacteriophage T7 RNA polymerase/promoter system for controlled exclusive expression of specific genes", Proc. Natl. Acad. Sci. U.S.A. 82:1074-78 (1985).

Van Ness & Chen, "The use of oligodeoxynucleotide probes in chaotrope based hybridization solutions", Nucleic Acids Res. vol. 19, No. 19, 5143-51 (1991).

Wick et al., "Evolution of Genomic Content in the Stepwise Emergence of *Escherichia coli* 0157:H7", Journal of Bacteriology, vol. 187, No. 5, 2005.

Yokoyama et al., "Complete nucleotide sequence of the prophage VT1-Sakai carrying the Shiga toxin 1 genes of the anterohmorrhagic *Escherichia coli* 0157:H7 strain derived from the Sakai outbreak", Gene, Elsevier, Amsterdam, NL, vol. 258, No. 1-2, 2000.

SEQUENCES AND THEIR USE FOR DETECTION AND CHARACTERIZATION OF E. COLI O157:H7

CROSS REFERENCE TO RELATED APPLICATIONS

This application claims priority of U.S. Provisional Application Ser. No. 61/767,458 filed Feb. 21, 2013, which is hereby incorporated by reference in its entirety.

FIELD OF INVENTION

The field of invention relates to methods for detection and characterization of *Escherichia coli* bacteria serotype O157:H7 based on the presence of nucleic acid sequences, preferably PCR-based methods for detection, and to oligonucleotide molecules and reagents and kits useful therefor.

BACKGROUND OF INVENTION

*Escherichia coli* is a gram-negative, rod-shaped bacterium. Although most strains of *E. coli* are benign and are found as normal intestinal flora of humans and other animals, some strains are pathogenic and can lead to disease. Different strains of pathogenic *E. coli* differ in their epidemiology, clinical course and potential for causing outbreaks of disease.

Pathogenicity has been linked to several serotypes, as defined by O and H antigens. Different pathogenic serotypes are associated with different clinical disease courses and have associated with them different levels of concern from the standpoint of public health. Several outbreaks of disease have been tracked to food and water borne sources of pathogenic *E. coli*.

One serotype of *E. coli* in particular, serotype O157:H7, has been associated with several food and water borne outbreaks and is regulated as an adulterant in ground beef by the U.S. Department of Agriculture (USDA) with a zero tolerance standard. This serotype of *E. coli* is believed to have arisen from an O55:H7 parent strain, which then switched from O55 to O157 upon the transfer into the progenitor O55:H7 genome of the large virulence plasmid pO157, which contained the O157-rfb gene cluster as well as some additional genetic information (see, e.g., Wick et al., J. Bacteriol. 187:1783-91 (2005)).

Since *E. coli* is ubiquitous, and since serotype O157:H7 is highly pathogenic and tightly regulated, the ability to specifically detect and characterize *E. coli* serotype O157:H7 in a sample, even in the presence of other *E. coli* serotypes, is useful.

Published U.S. Patent Application No. 2011/0020823 and Sharma (Mol. Cell. Probes 20:298-306 (2006)) both teach the detection of *E. coli* O157:H7 through the simultaneous amplification of two sequence targets, neither of which is unique to *E. coli* O157:H7. However, the presence of both targets within a single strain is indicative of *E. coli* O157:H7. A problem arises when the sample being tested is not a pure culture, which is often the case in *E. coli* infections. In this case, it is possible for two different strains each to contribute one target for PCR amplification. Since both targets amplify, the response is erroneously interpreted as an *E. coli* O157:H7 response.

There is therefore a need for a method of detecting *E. coli* O157:H7 that does not potentially lead to false positive results.

SUMMARY OF INVENTION

One aspect is for a method for detecting the presence of *E. coli* O157:H7 in a sample, said sample comprising nucleic acids, said method comprising: (a) providing a reaction mixture comprising a primer pair selected from the group consisting of primer pair SEQ ID NO:1 and SEQ ID NO:2, primer pair SEQ ID NO:3 and SEQ ID NO:4, primer pair SEQ ID NO:5 and SEQ ID NO:6, primer pair SEQ ID NO:7 and SEQ ID NO:8, and a combination thereof; (b) performing PCR amplification of said nucleic acids of said sample using the reaction mixture of step (a); and (c) detecting the amplification of step (b), whereby a positive detection of amplification indicates the presence of *E. coli* O157:H7 in the sample.

Another aspect is for an isolated polynucleotide comprising a nucleotide sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, and SEQ ID NO:18.

A further aspect is for a replication composition for use in performance of PCR, comprising: (a) a primer pair selected from the group consisting of primer pair SEQ ID NO:1 and SEQ ID NO:2, primer pair SEQ ID NO:3 and SEQ ID NO:4, primer pair SEQ ID NO:5 and SEQ ID NO:6, primer pair SEQ ID NO:7 and SEQ ID NO:8, and a combination thereof; and (b) thermostable DNA polymerase.

An additional aspect is for a kit for detection of *E. coli* O157:H7 in a sample, comprising the aforementioned replication composition.

A further aspect is for a tablet comprising the aforementioned replication composition.

Other objects and advantages will become apparent to those skilled in the art upon reference to the detailed description that hereinafter follows.

SUMMARY OF THE SEQUENCES

The sequences conform with 37 C.F.R. §§1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO:1 is a forward primer for detection of *E. coli* O157:H7.

SEQ ID NO:2 is a reverse primer for detection of *E. coli* O157:H7.

SEQ ID NO:3 is a forward primer for detection of *E. coli* O157:H7.

SEQ ID NO:4 is a reverse primer for detection of *E. coli* O157:H7.

SEQ ID NO:5 is a forward primer for detection of *E. coli* O157:H7.

SEQ ID NO:6 is a reverse primer for detection of *E. coli* O157:H7.

SEQ ID NO:7 is a forward primer for detection of *E. coli* O157:H7.

SEQ ID NO:8 is a reverse primer for detection of *E. coli* O157:H7.

SEQ ID NO:9 is a probe for use in the detection of *E. coli* O157:H7. In one embodiment, the probe is 5'-labeled with a fluorescent dye. In some embodiments, the 3' terminus of SEQ ID NO:9 is attached to the 5' terminus of one of the primers listed above, preferably SEQ ID NO:1, via a suitable linker moiety, such as an 18-carbon spacer.

SEQ ID NO:10 is a probe for use in the detection of *E. coli* O157:H7. In one embodiment, the probe is 5'-labeled with a fluorescent dye. In some embodiments, the 3' terminus of SEQ ID NO:10 is attached to the 5' terminus of one of the primers listed above, preferably SEQ ID NO:2, via a suitable linker moiety, such as an 18-carbon spacer.

SEQ ID NO:11 is a probe for use in the detection of *E. coli* O157:H7. In one embodiment, the probe is 5'-labeled with a fluorescent dye. In some embodiments, the 3' terminus of SEQ ID NO:11 is attached to the 5' terminus of one of the primers listed above, preferably SEQ ID NO:4, via a suitable linker moiety, such as an 18-carbon spacer.

SEQ ID NO:12 is a probe for use in the detection of *E. coli* O157:H7. In one embodiment, the probe is 5'-labeled with a fluorescent dye. In some embodiments, the 3' terminus of SEQ ID NO:12 is attached to the 5' terminus of one of the primers listed above, preferably SEQ ID NO:6, via a suitable linker moiety, such as an 18-carbon spacer.

SEQ ID NO:13 is a probe for use in the detection of *E. coli* O157:H7. In one embodiment, the probe is 5'-labeled with a fluorescent dye. In some embodiments, the 3' terminus of SEQ ID NO:13 is attached to the 5' terminus of one of the primers listed above, preferably SEQ ID NO:7, via a suitable linker moiety, such as an 18-carbon spacer.

SEQ ID NO:14 is a blocking oligonucleotide capable of hybridizing to the probe of SEQ ID NO:9. In one embodiment, this blocking oligonucleotide is 3'-labeled with a fluorescent dye.

SEQ ID NO:15 is a blocking oligonucleotide capable of hybridizing to the probe of SEQ ID NO:10. In one embodiment, this blocking oligonucleotide is 3'-labeled with a fluorescent dye.

SEQ ID NO:16 is a blocking oligonucleotide capable of hybridizing to the probe of SEQ ID NO:11. In one embodiment, this blocking oligonucleotide is 3'-labeled with a fluorescent dye.

SEQ ID NO:17 is a blocking oligonucleotide capable of hybridizing to the probe of SEQ ID NO:12. In one embodiment, this blocking oligonucleotide is 3'-labeled with a fluorescent dye.

SEQ ID NO:18 is a blocking oligonucleotide capable of hybridizing to the probe of SEQ ID NO:13. In one embodiment, this blocking oligonucleotide is 3'-labeled with a fluorescent dye.

SEQ ID NO:19 is an SV40 (SV4222) control primer.

SEQ ID NO:20 is an SV40 (SV4312) control primer.

SEQ ID NO:21 is an SV40 Scorpion control probe, preferably 5'-labeled with tetramethylrhodamine (TAMRA) and containing a BHQ-2™ label and 18-carbon spacer between bases 52 and 53.

DETAILED DESCRIPTION OF PREFERRED EMBODIMENTS

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Definitions

In this disclosure, a number of terms and abbreviations are used. The following definitions are provided.

As used herein, the term "about" or "approximately" means within 20%, preferably within 10%, and more preferably within 5% of a given value or range.

The term "comprising" is intended to include embodiments encompassed by the terms "consisting essentially of" and "consisting of". Similarly, the term "consisting essentially of" is intended to include embodiments encompassed by the term "consisting of".

The term "pO157 portion" refers to the area of the *E. coli* O157:H7 genome identified, for example, in Wick et al., J. Bacteriol. 187:1783-91 (2005), as being divergent from the O55:H7 progenitor strain and as having been transferred into the progenitor strain to create the O157:H7 *E. coli* serotype. This region includes, among other things, the O157-rfb gene cluster, colonic acid biosynthesis genes, and putative type-1 fimbrial protein genes.

"Polymerase chain reaction" is abbreviated PCR.

The term "isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The terms "polynucleotide", "polynucleotide sequence", "nucleic acid sequence", and "nucleic acid fragment" are used interchangeably herein. These terms encompass nucleotide sequences and the like. A polynucleotide may be a polymer of RNA or DNA that is single- or double-stranded, that optionally contains synthetic, non-natural, or altered nucleotide bases. A polynucleotide in the form of a polymer of DNA may be comprised of one or more strands of cDNA, genomic DNA, synthetic DNA, or mixtures thereof.

The term "amplification product" refers to nucleic acid fragments produced during a primer-directed amplification reaction. Typical methods of primer-directed amplification include polymerase chain reaction (PCR), ligase chain reaction (LCR), or strand displacement amplification (SDA). If PCR methodology is selected, the replication composition may comprise the components for nucleic acid replication, for example: nucleotide triphosphates, two (or more) primers with appropriate sequences, thermostable polymerase, buffers, solutes, and proteins. These reagents and details describing procedures for their use in amplifying nucleic acids are provided in U.S. Pat. Nos. 4,683,202 and 4,683,195, incorporated herein by reference. If LCR methodology is selected, then the nucleic acid replication compositions may comprise, for example: a thermostable ligase (e.g., *Thermus aquaticus* ligase), two sets of adjacent oligonucleotides (wherein one member of each set is complementary to each of the target strands), Tris-HCl buffer, KCl, EDTA, NAD, dithiothreitol, and salmon sperm DNA. See, e.g., Tabor et al., Proc. Natl. Acad. Sci. U.S.A. 82:1074-78 (1985).

The term "primer" refers to an oligonucleotide (synthetic or occurring naturally) that is capable of acting as a point of initiation of nucleic acid synthesis or replication along a complementary strand when placed under conditions in which synthesis of a complementary strand is catalyzed by a polymerase. A primer can further contain a detectable label, for example a 5' end label.

The term "probe" refers to an oligonucleotide (synthetic or occurring naturally) that is complementary (though not necessarily fully complementary) to a polynucleotide of interest and forms a duplexed structure by hybridization with at least one strand of the polynucleotide of interest. A probe or primer-probe complex can further contain a detectable label.

A probe can either be an independent entity or complexed with or otherwise attached to a primer, such as where a probe is connected via its 3' terminus to a primer's 5' terminus through a linker, which may be a nucleotide or non-nucleotide linker and which may be a non-amplifiable linker, such as a hexethylene glycol (HEG) or 18-carbon linker. In such a case, this would be termed a "primer-probe complex". One example of such a primer-probe complex can be found in U.S. Pat. No. 6,326,145, incorporated herein by reference in its entirety, which are frequently referred to as "Scorpion probes" or "Scorpion primers".

As used herein, the terms "label" and "detectable label" refer to a molecule capable of detection, including, but not limited to, radioactive isotopes, fluorescers, chemiluminescers, enzymes, enzyme substrates, enzyme cofactors, enzyme inhibitors, chromophores, dyes, metal ions, metal sols, semiconductor nanocrystals, ligands (e.g., biotin, avidin, streptavidin, or haptens), and the like. A detectable label can also include a combination of a reporter and a quencher.

The term "reporter" refers to a substance or a portion thereof which is capable of exhibiting a detectable signal, which signal can be suppressed by a quencher. The detectable signal of the reporter is, e.g., fluorescence in the detectable range. The term "quencher" refers to a substance or portion thereof which is capable of suppressing, reducing, inhibiting, etc., the detectable signal produced by the reporter.

As used herein, the terms "quenching" and "fluorescence energy transfer" refer to the process whereby, when a reporter and a quencher are in close proximity, and the reporter is excited by an energy source, a substantial portion of the energy of the excited state nonradiatively transfers to the quencher where it either dissipates nonradiatively or is emitted at a different emission wavelength than that of the reporter.

Preferably, the reporter may be selected from fluorescent organic dyes modified with a suitable linking group for attachment to the oligonucleotide, such as to the terminal 3' carbon or terminal 5' carbon. The quencher may also be selected from organic dyes, which may or may not be fluorescent, depending on the embodiment of the present invention. Generally, whether the quencher is fluorescent or simply releases the transferred energy from the reporter by non-radiative decay, the absorption band of the quencher should at least substantially overlap the fluorescent emission band of the reporter to optimize the quenching. Non-fluorescent quenchers or dark quenchers typically function by absorbing energy from excited reporters, but do not release the energy radiatively.

Selection of appropriate reporter-quencher pairs for particular probes may be undertaken in accordance with known techniques. Fluorescent and dark quenchers and their relevant optical properties from which exemplary reporter-quencher pairs may be selected are listed and described, for example, in Berlman, Handbook of Fluorescence Spectra of Aromatic Molecules, 2nd ed., Academic Press, New York, 1971, the content of which is incorporated herein by reference. Examples of modifying reporters and quenchers for covalent attachment via common reactive groups that can be added to an oligonucleotide in the present invention may be found, for example, in Haugland, Handbook of Fluorescent Probes and Research Chemicals, Molecular Probes of Eugene, Oreg., 1992, the content of which is incorporated herein by reference.

Preferred reporter-quencher pairs may be selected from xanthene dyes including fluoresceins and rhodamine dyes. Many suitable forms of these compounds are available commercially with substituents on the phenyl groups, which can be used as the site for bonding or as the bonding functionality for attachment to an oligonucleotide. Another preferred group of fluorescent compounds for use as reporters are the naphthylamines, having an amino group in the alpha or beta position. Included among such naphthylamino compounds are 1-dimethylaminonaphthyl-5 sulfonate, 1-anilino-8-naphthalene sulfonate and 2-p-touidinyl-6-naphthalene sulfonate. Other dyes include 3-phenyl-7-isocyanatocoumarin; acridines such as 9-isothiocyanatoacridine; N-(p-(2-benzoxazolyl)phenyl)maleimide; benzoxadiazoles; stilbenes; pyrenes and the like.

Most preferably, the reporters and quenchers are selected from fluorescein and rhodamine dyes. These dyes and appropriate linking methodologies for attachment to oligonucleotides are well known in the art.

Suitable examples of quenchers may be selected from 6-carboxy-tetramethyl-rhodamine, 4-(4-dimethylaminophenylazo)benzoic acid (DABYL), tetramethyirhodamine (TAMRA), BHQ-0™, BHQ-1™, BHQ-2™, and BHQ-3™, each of which are available from Biosearch Technologies, Inc. of Novato, Calif., QSY-7™, QSY-9™, QSY-21™ and QSY-35™, each of which are available from Molecular Probes, Inc., and the like.

Suitable examples of reporters may be selected from dyes such as SYBR green, 5-carboxyfluorescein (5-FAM™ available from Applied Biosystems of Foster City, Calif.), 6-carboxyfluorescein (6-FAM, tetrachloro-6-carboxyfluorescein (TET), 2,7-dimethoxy-4,5-dichloro-6-carboxyfluorescein, hexachloro-6-carboxyfluorescein (HEX), 6-carboxy-2',4,7,7'-tetrachlorofluorescein (6-TET™ available from Applied Biosystems), carboxy-X-rhodamine (ROX), 6-carboxy-4',5'-dichloro-2',7'-dimethoxyfluorescein (6-JOE™ available from Applied Biosystems), VIC™ dye products available from Molecular Probes, Inc., NED™ dye products available from available from Applied Biosystems, and the like.

One example of a probe which contains a reporter and a quencher is a Scorpion probe in either a unimolecular or bimolecular conformation. In a unimolecular Scorpion, the probe portion of the primer-probe complex is flanked by self-complementary regions which allow the probe to form into a stem-loop structure when the probe is unbound from its target DNA. Examples of such self-complementary regions can be found in SEQ ID NO:9 and SEQ ID NO:14, SEQ ID NO:10 and SEQ ID NO:15, SEQ ID NO:11 and SEQ ID NO:16, SEQ ID NO:12 and SEQ ID NO:17, and SEQ ID NO:13 and SEQ ID NO:18. Further, in a unimolecular Scorpion, a reporter is typically attached at or near one of the self-complementary regions, such as at the 5' terminus of the Scorpion probe, and a quencher is attached at or near the other self-complementary region, such as immediately 5' to the non-amplifiable linker, such that the quencher is in sufficiently close proximity to the reporter to cause quenching when the probe is in its stem-loop conformation. In a bimolecular Scorpion, self-complementary flanking regions are not typically employed, but rather a separate "blocking oligonucleotide" is employed in conjunction with the Scorpion probe. This blocking oligonucleotide is capable of hybridizing to the probe region of the Scorpion probe when the probe is unbound from its target DNA. An example of a bimolecular Scorpion pair is SEQ ID NO:9 (the Scorpion probe) and SEQ ID NO:14 (the blocking oligonucleotide). Further, in a bimolecular Scorpion, the reporter is typically attached to the probe region of the Scorpion probe, such as at the 5' terminus of the Scorpion probe, while the quencher is attached to the blocking oligonucleotide, such as at the 3' terminus of the blocking oligonucleotide, such that the quencher is in sufficiently close proximity to the reporter to cause quenching when the probe is unbound from its target DNA and is instead hybridized to the blocking oligonucleotide.

Another example of a probe which contains a reporter and a quencher is a probe that is to be used in a 5'-exonuclease assay, such as the Taqman® real-time PCR technique. In this context, the oligonucleotide probe will have a sufficient number of phosphodiester linkages adjacent to its 5' end so that the 5' to 3' nuclease activity employed can efficiently degrade the bound probe to separate the reporters and quenchers. Yet another example of a probe which contains a reporter and quencher is a Molecular Beacon type probe, which contains a probe region flanked by self-complementary regions that allow the probe to form a stem-loop structure when unbound from the probe's target sequence. Such probes typically have a reporter attached at or near one terminus and a quencher attached at or near the other terminus such that the quencher is in sufficiently close proximity to the reporter to cause quenching when the probe is in its unbound, and thus stem-loop, form.

The term "replication inhibitor moiety" refers to any atom, molecule or chemical group that is attached to the 3' terminal hydroxyl group of an oligonucleotide that will block the initiation of chain extension for replication of a nucleic acid strand. Examples include, but are not limited to: 3'-deoxynucleotides (e.g., cordycepin), dideoxynucleotides, phosphate, ligands (e.g., biotin and dinitrophenol), reporter molecules (e.g., fluorescein and rhodamine), carbon chains (e.g., propanol), a mismatched nucleotide or polynucleotide, or peptide nucleic acid units. The term "non-participatory" refers to the lack of participation of a probe or primer in a reaction for the amplification of a nucleic acid molecule. Specifically a non-participatory probe or primer is one that will not serve as a substrate for, or be extended by, a DNA or RNA polymerase. A "non-participatory probe" is inherently incapable of being chain extended by a polymerase. It may or may not have a replication inhibitor moiety.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified, for example, in Sambrook, J., Fritsch, E. F. and Maniatis, T., *Molecular Cloning: A Laboratory Manual*, 2nd ed., Cold Spring Harbor Laboratory: Cold Spring Harbor, N.Y. (1989), particularly Chapter 11 and Table 11.1 therein (entirely incorporated herein by reference). The conditions of temperature and ionic strength determine the "stringency" of the hybridization. For preliminary screening for homologous nucleic acids, low stringency hybridization conditions, corresponding to a Tm of 55° C., can be used, e.g., 5×SSC, 0.1% SDS, 0.25% milk, and no formamide; or 30% formamide, 5×SSC, 0.5% SDS. Moderate stringency hybridization conditions correspond to a higher Tm, e.g., 40% formamide, with 5× or 6×SSC. Hybridization requires that the two nucleic acids contain complementary sequences, although, depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one preferred embodiment, the length for a hybridizable nucleic acid is at least about 10 nucleotides. More preferably a minimum length for a hybridizable nucleic acid is at least about 11 nucleotides, at least about 12 nucleotides, at least about 13 nucleotides, at least about 14 nucleotides, at least about 15 nucleotides, at least about 16 nucleotides, at least about 17 nucleotides, at least about 18 nucleotides, at least about 19 nucleotides, at least about 20 nucleotides, at least about 21 nucleotides, at least about 22 nucleotides, at least about 23 nucleotides, at least about 24 nucleotides, at least about 25 nucleotides, at least about 26 nucleotides, at least about 27 nucleotides, at least about 28 nucleotides, at least about 29 nucleotides, or, most preferably, at least 30 nucleotides. Furthermore, the skilled artisan will recognize that the temperature and wash solution salt concentration may be adjusted as necessary according to factors such as length of the probe.

Standard recombinant DNA and molecular cloning techniques used here are well known in the art and are described by, e.g., Sambrook et al. (supra); and by Ausubel, F. M. et al., *Current Protocols in Molecular Biology*, published by Greene Publishing Assoc. and Wiley-Interscience (1987).

Genome Detection Regions

Applicants have solved the stated problem through a method that uses a pair of phage protein sequences which are only contiguous and amplifiable in *E. coli* O157:H7. The use of this target will not result in a false positive response for mixed cultures, where two different strains each contribute one PCR target.

As discussed above, *E. coli* O157:H7 came about via the transfer of the pO157 plasmid into the O55:H7 progenitor strain. Thus, *E. coli* O157:H7 possesses a pO157 portion within the bacterial genome. It has been found that the detection of a combination of regions both within and outside this pO157 portion of the *E. coli* O157:H7 genome produces a sensitive and accurate method of detecting *E. coli* O157:H7, even in a background of other serotypes of *E. coli*.

The present invention therefore relates to detection and identification of *E. coli* O157:H7 through the detection of the presence of a pair of contiguous phage protein sequences. These sequences are only contiguous in *E. coli*

O157:H7 and will not amplify in mixed cultures of non-*E. coli* O157:H7 strains under the specified amplification conditions.

The present detection method finds utility in detection of *E. coli* O157:H7 in any type of sample, for example in appropriate samples for food testing, environmental testing, or human or animal diagnostic testing. While examples of suitable methods for detecting these regions are included herein, it is to be understood that the invention is not limited to the methods described. Rather any suitable method can be employed to detect these DNA regions and subsequently the *E. coli* itself.

Oligonucleotides

Oligonucleotides of the instant invention are set forth in SEQ ID NOs: 1-18.

Oligonucleotides of the instant invention may be used as primers for PCR amplification. Preferred primer pairs and their corresponding targets, blocking oligonucleotides, and probes are shown in Table 1.

TABLE 1

| 5' (Forward) Primer | Blocking Oligonucleotide | 3' (Reverse) Primer | Probe |
|---|---|---|---|
| SEQ ID NO: 1 | SEQ ID NO: 14 | SEQ ID NO: 2 | SEQ ID NO: 9 |
| SEQ ID NO: 1 | SEQ ID NO: 15 | SEQ ID NO: 2 | SEQ ID NO: 10 |
| SEQ ID NO: 3 | SEQ ID NO: 16 | SEQ ID NO: 4 | SEQ ID NO: 11 |
| SEQ ID NO: 5 | SEQ ID NO: 17 | SEQ ID NO: 6 | SEQ ID NO: 12 |
| SEQ ID NO: 7 | SEQ ID NO: 18 | SEQ ID NO: 8 | SEQ ID NO: 13 |

These oligonucleotide primers may also be useful for other nucleic acid amplification methods such as the ligase chain reaction (LCR) (EP 0 320 308; Carrino et al., J. Microbiol. Methods 23:3-20 (1995)); nucleic acid sequence-based amplification (NASBA) (Carrino et al., 1995, supra); and self-sustained sequence replication (3SR) and "Q replicase amplification" (Pfeffer et al., Vet. Res. Commun. 19:375-407 (1995)).

The oligonucleotide primers of the present invention can also contain a detectable label, for example a 5' end label.

In addition, oligonucleotides of the present invention also may be used as hybridization probes. Preferred hybridization probes are SEQ ID NOs: 9 and 10. Hybridization using DNA probes has been frequently used for the detection of pathogens in food, clinical and environmental samples, and the methodologies are generally known to one skilled in the art. It is generally recognized that the degree of sensitivity and specificity of probe hybridization is lower than that achieved through the previously described amplification techniques. The nucleic acid probes of the present invention can also possess a detectable label, such as a reporter-quencher combination as are employed in Scorpion probe assays or in 5'-exonuclease detection assays, such as the Taqman® assay.

The 3' terminal nucleotide of the nucleic acid probe may be rendered incapable of extension by a nucleic acid polymerase in one embodiment of the invention. Such blocking may be carried out, for example by the attachment of a replication inhibitor moiety, such as a reporter or quencher, to the terminal 3' carbon of the nucleic acid probe by a linking moiety, or by making the 3'-terminal nucleotide a dideoxynucleotide. Alternatively, the 3' end of the nucleic acid probe may be rendered impervious to the 3' to 5' extension activity of a polymerase by incorporating one or more modified internucleotide linkages onto the 3' end of the oligonucleotide. Minimally, the 3' terminal internucleotide linkage must be modified, however, additional internucleotide linkages may be modified. Internucleotide modifications which prevent elongation from the 3' end of the nucleic acid probe and/or which block the 3' to 5' exonuclease activity of the DNA polymerase during PCR may include phosphorothioate linkages, methylphosphonate linkages, boranophosphate linkages, and other similar polymerase-resistant internucleotide linkages. An alternative method to block 3' extension of the probe is to form an adduct at the 3' end of the probe using mitomycin C or other like antitumor antibiotics such as described in Basu et al., Biochemistry 32:4708-18 (1993). Thus, the precise mechanism by which the 3' end of the nucleic acid probe is protected from cleavage is not essential so long as the quencher is not cleaved from the nucleic acid probe.

A nucleic acid probe sequence can also optionally be employed with the primer sequence pairs of the present invention in an amplification based detection technique, such as in the 3'-exonuclease assay. Preferred primer/probe combinations are indicated in Table 1.

Preferably, SEQ ID NOs:9-13 are 5' end-labeled with a Calfluor Gold 540 reporter and its corresponding quenchers (SEQ ID NOs:14-18, respectively) possess a BHQ1 label at or near the 3' end (e.g., attached to nucleotide 26 of SEQ ID NO:14, nucleotide 28 of SEQ ID NO:15, nucleotide 23 of SEQ ID NO:16, nucleotide 22 of SEQ ID NO:17, and nucleotide 23 of SEQ ID NO:18).

Some oligonucleotides of the present invention contain both primer and probe regions, and thus can be employed as a primer-probe complex in an appropriate assay, such as a Scorpion probe assay. These primer probe complexes of the instant invention contain a non-amplifiable linker that connects the 3' terminus of the probe region to the 5' terminus of the primer region. This non-amplifiable linker stops extension of a complementary strand from proceeding into the probe region of the primer-probe complex. Examples of such non-amplifiable linkages include hexethylene glycol (HEG) and, preferably, 18-carbon linkers. Primer-probe complexes of the present invention can also contain a self-complementary region that allows the primer-probe complex to form a stem-loop structure when the probe is unbound from its target DNA, which may be useful, for example, in bringing the reporter and quencher into sufficiently close proximity to one another to cause the reporter signal to be quenched. Examples of such primer-probe complexes with self-complementary regions include SEQ ID NO:9 linked to SEQ ID NO:1 with an 18-carbon spacer, SEQ ID NO:10 linked to SEQ ID NO:2 with an 18-carbon spacer, SEQ ID NO:11 linked to SEQ ID NO:4 with an 18-carbon spacer, SEQ ID NO:12 linked to SEQ ID NO:6 with an 18-carbon spacer, SEQ ID NO:13 linked to SEQ ID NO:7 with an 18-carbon spacer.

Assay Methods

Detection of the presence of *E. coli* O157:H7 itself, may be accomplished in any suitable manner. Preferred methods are primer-directed amplification methods and nucleic acid hybridization methods. These methods may be used to detect *E. coli* O157:H7 in a sample that is either a complex matrix or a purified culture, e.g., from an animal, environmental, or food source suspected of contamination.

A preferred embodiment of the instant invention comprises (1) culturing a complex sample mixture in a non-selective growth media to resuscitate the target bacteria, (2) releasing total target bacterial DNA, and (3) subjecting the total DNA to an amplification protocol with a primer pair of the invention and optionally with a nucleic acid probe comprising a detectable label.

Primer-Directed Amplification Assay Methods

A variety of primer-directed nucleic acid amplification methods are known in the art which can be employed in the present invention, including thermal cycling methods (e.g., PCR, RT-PCR, and LCR), as well as isothermal methods and strand displacement amplification (SDA). The preferred method is PCR.

Sample Preparation:

The oligonucleotides and methods according to the instant invention may be used directly with any suitable clinical or environmental samples, without any need for sample preparation. In order to achieve higher sensitivity, and in situations where time is not a limiting factor, it is preferred that the samples be pre-treated and that pre-amplification enrichment is performed.

The minimum industry standard for the detection of food-borne bacterial pathogens is a method that will reliably detect the presence of one pathogen cell in 25 g of food matrix as described in Andrews et al., 1984, "Food Sample and Preparation of Sample Homogenate", Chapter 1 in *Bacteriological Analytical Manual*, 8th Edition, Revision A, Association of Official Analytical Chemists, Arlington, Va. In order to satisfy this stringent criterion, enrichment methods and media have been developed to enhance the growth of the target pathogen cell in order to facilitate its detection by biochemical, immunological or nucleic acid hybridization means. Typical enrichment procedures employ media that will enhance the growth and health of the target bacteria and also inhibit the growth of any background or non-target microorganisms present. For example, the USDA has set forth a protocol for enrichment of samples of ground beef to be tested for pathogenic *E. coli* (U.S. Food and Drug Administration, Bacterial Analytical Manual).

Selective media have been developed for a variety of bacterial pathogens and one of skill in the art will know to select a medium appropriate for the particular organism to be enriched, e.g. *E. coli* O157:H7. A general discussion and recipes of non-selective media are described in the FDA Bacteriological Analytical Manual. (1998) published and distributed by the Association of Analytical Chemists, Suite 400, 2200 Wilson Blvd, Arlington, Va. 22201-3301.

After selective growth, a sample of the complex mixtures is removed for further analysis. This sampling procedure may be accomplished by a variety of means well known to those skilled in the art. In a preferred embodiment, 5 µl of the enrichment culture is removed and added to 200 µl of lysis solution containing protease. The lysis solution is heated at 37° C. for 20 min followed by protease inactivation at 95° C. for 10 min as described in the BAX® System User's Guide, DuPont Qualicon, Inc., Wilmington, Del.

PCR Assay Methods:

A preferred method for detecting the presence of *E. coli* O157:H7 in a sample comprises (a) performing PCR amplification using primer pairs listed in Table 1 to produce a PCR amplification result; and (b) detecting the amplification, whereby a positive detection of the amplification indicates the presence of *E. coli* O157:H7 in the sample.

In another preferred embodiment, prior to performing PCR amplification, a step of preparing the sample may be carried out. The preparing step may comprise at least one of the following processes: (1) bacterial enrichment, (2) separation of bacterial cells from the sample, (3) cell lysis, and (4) total DNA extraction.

Amplification Conditions:

A skilled person will understand that any generally acceptable PCR conditions may be used for successfully detecting *E. coli* O157:H7 bacteria using the oligonucleotides of the instant invention, and depending on the sample to be tested and other laboratory conditions, routine optimization for the PCR conditions may be necessary to achieve optimal sensitivity and specificity. Optimally, they achieve PCR amplification results from all of the intended specific targets while giving no PCR results for other, non-target species.

Detection/Examination/Analysis:

Primer-directed amplification products can be analyzed using various methods. Homogenous detection refers to a preferred method for the detection of amplification products where no separation (such as by gel electrophoresis) of amplification products from template or primers is necessary. Homogeneous detection is typically accomplished by measuring the level of fluorescence of the reaction mixture during or immediately following amplification. In addition, heterogeneous detection methods, which involve separation of amplification products during or prior to detection, can be employed in the present invention.

Homogenous detection may be employed to carry out "real-time" primer-directed nucleic acid amplification and detection, using primer pairs of the instant invention (e.g., "real-time" PCR and "real-time" RT-PCR). Preferred "real-time" methods are set forth in U.S. Pat. Nos. 6,171,785, 5,994,056, 6,326,145, 5,804,375, 5,538,848, 5,487,972, and 5,210,015, each of which is hereby incorporated by reference in its entirety.

A particularly preferred "real-time" detection method is the Scorpion probe assay as set forth in U.S. Pat. No. 6,326,145, which is hereby incorporated by reference in its entirety. In the Scorpion probe assay, PCR amplification is performed using a Scorpion probe (either unimolecular or bimolecular) as a primer-probe complex, the Scorpion probe possessing an appropriate reporter-quencher pair to allow the detectable signal of the reporter to be quenched prior to elongation of the primer. Post-elongation, the quenching effect is eliminated and the amount of signal present is quantitated. As the amount of amplification product increases, an equivalent increase in detectable signal will be observed, thus allowing the amount of amplification product present to be determined as a function of the amount of detectable signal measured. When more than one Scorpion probe is employed in a Scorpion probe assay each probe can have a different detectable label (e.g., reporter-quencher pair) attached, thus allowing each probe to be detected independently of the other probes.

Another preferred "real-time" detection method is the 5'-exonuclease detection method, as set forth in U.S. Pat. Nos. 5,804,375, 5,538,848, 5,487,972, and 5,210,015, each of which is hereby incorporated by reference in its entirety. In the 5'-exonuclease detection assay a modified probe is employed during PCR which binds intermediate to or between the two members of the amplification primer pair. The modified probe possesses a reporter and a quencher and is designed to generate a detectable signal to indicate that it has hybridized with the target nucleic acid sequence during PCR. As long as both the reporter and the quencher are on the probe, the quencher stops the reporter from emitting a detectable signal. However, as the polymerase extends the primer during amplification, the intrinsic 5' to 3' nuclease activity of the polymerase degrades the probe, separating the reporter from the quencher, and enabling the detectable signal to be emitted. Generally, the amount of detectable signal generated during the amplification cycle is proportional to the amount of product generated in each cycle.

It is well known that the efficiency of quenching is a strong function of the proximity of the reporter and the quencher, i.e., as the two molecules get closer, the quenching efficiency increases. As quenching is strongly dependent on the physical proximity of the reporter and quencher, the reporter and the quencher are preferably attached to the probe within a few nucleotides of one another, usually within 30 nucleotides of one another, more preferably with a separation of from about 6 to 16 nucleotides. Typically, this separation is achieved by attaching one member of a reporter-quencher pair to the 5' end of the probe and the other member to a nucleotide about 6 to 16 nucleotides away.

Again, when more than one Taqman® probe is employed in a 5'-exonuclease detection assay, each probe can have a different detectable label (e.g., reporter-quencher pair) attached, thus allowing each probe to be detected independently of the other probes.

Another preferred method of homogenous detection involves the use of DNA melting curve analysis, particularly with the BAX® System hardware and reagent tablets from DuPont Qualicon Inc. The details of the system are given in U.S. Pat. No. 6,312,930 and PCT Publication Nos. WO 97/11197 and WO 00/66777, each of which is hereby incorporated by reference in its entirety.

Melting curve analysis detects and quantifies double stranded nucleic acid molecule ("dsDNA" or "target") by monitoring the fluorescence of the target amplification product ("target amplicon") during each amplification cycle at selected time points.

As is well known to the skilled artisan, the two strands of a dsDNA separate or melt, when the temperature is higher than its melting temperature. Melting of a dsDNA molecule is a process, and under a given solution condition, melting starts at a temperature (designated Tms hereinafter), and completes at another temperature (designated Tme hereinafter). The familiar term, Tm, designates the temperature at which melting is 50% complete.

A typical PCR cycle involves a denaturing phase where the target dsDNA is melted, a primer annealing phase where the temperature optimal for the primers to bind to the now-single-stranded target, and a chain elongation phase (at a temperature Te) where the temperature is optimal for DNA polymerase to function.

According to the present invention, Tms should be higher than Te, and Tme should be lower (often substantially lower) than the temperature at which the DNA polymerase is heat-inactivated. Melting characteristics are affected by the intrinsic properties of a given dsDNA molecule, such as deoxynucleotide composition and the length of the dsDNA.

Intercalating dyes will bind to double stranded DNA. The dye/dsDNA complex will fluoresce when exposed to the appropriate excitation wavelength of light, which is dye dependent, and the intensity of the fluorescence may be proportionate to concentration of the dsDNA. Methods taking advantage of the use of DNA intercalating dyes to detect and quantify dsDNA are known in the art. Many dyes are known and used in the art for these purposes. The instant methods also take advantage of such relationship.

Examples of such intercalating dyes include, but are not limited to, SYBR Green-I®, ethidium bromide, propidium iodide, TOTO®-1 {Quinolinium, 1-1'-[1,3-propanediylbis [(dimethyl iminio)-3,1-propanediyl]]bis[4-[(3-methyl-2 (3H)-benzothiazolylidene)methyl]]-, tetraiodide}, and YoPro® {Quinolinium, 4-[(3-methyl-2(3H)-benzoxazolylidene)methyl]-1-[3-(trimethylammonio)-propyl]-,di-iodide}. Most preferred for the instant invention is a non-asymmetrical cyanide dye such as SYBR Green-I®, manufactured by Molecular Probes, Inc. (Eugene, Oreg.).

Melting curve analysis is achieved by monitoring the change in fluorescence while the temperature is increased. When the temperature reaches the $T_{MS}$ specific for the target amplicon, the dsDNA begins to denature. When the dsDNA denatures, the intercalating dye dissociates from the DNA and fluorescence decreases. Mathematical analysis of the negative of the change of the log of fluorescence divided by the change in temperature plotted against the temperature results in the graphical peak known as a melting curve.

It should be understood that the present invention could be operated using a combination of these techniques, such as by having a Scorpion probe directed to one target region and a Taqman® probe directed to a second target region. It should also be understood that the invention is not limited to the above described techniques. Rather, one skilled in the art would recognize that other techniques for detecting amplification as known in the art may also be used. For example, techniques such as PCR-based quantitative sequence detection (QSD) may be performed using nucleic acid probes which, when present in the single-stranded state in solution, are configured such that the reporter and quencher are sufficiently close to substantially quench the reporter's emission. However, upon hybridization of the intact reporter-quencher nucleic acid probe with the amplified target nucleic acid sequence, the reporter and quenchers become sufficiently distant from each other. As a result, the quenching is substantially abated causing an increase in the fluorescence emission detected.

In addition to homogenous detection methods, a variety of other heterogeneous detection methods are known in the art which can be employed in the present invention, including standard non-denaturing gel electrophoresis (e.g., acrylamide or agarose), denaturing gradient gel electrophoresis, and temperature gradient gel electrophoresis. Standard non-denaturing gel electrophoresis is a simple and quick method of PCR detection, but may not be suitable for all applications.

Denaturing Gradient Gel Electrophoresis (DGGE) is a separation method that detects differences in the denaturing behavior of small DNA fragments (200-700 bp). The principle of the separation is based on both fragment length and nucleotide sequence. In fragments that are the same length, a difference as little as one base pair can be detected. This is in contrast to non-denaturing gel electrophoresis, where DNA fragments are separated only by size. This limitation of non-denaturing gel electrophoresis results because the difference in charge density between DNA molecules is near neutral and plays little role in their separation. As the size of the DNA fragment increases, its velocity through the gel decreases.

DGGE is primarily used to separate DNA fragments of the same size based on their denaturing profiles and sequence. Using DGGE, two strands of a DNA molecule separate, or melt, when heat or a chemical denaturant is applied. The denaturation of a DNA duplex is influenced by two factors: 1) the hydrogen bonds formed between complimentary base pairs (since GC rich regions melt at higher denaturing conditions than regions that are AT rich); and 2) the attraction between neighboring bases of the same strand, or "stacking". Consequently, a DNA molecule may have several melting domains with each of their individual characteristic denaturing conditions determined by their nucleotide sequence. DGGE exploits the fact that otherwise identical DNA molecules having the same length and DNA sequence, with the exception of only one nucleotide within a specific denaturing domain, will denature at different temperatures or Tm. Thus, when the double-stranded (ds) DNA fragment is electrophoresed through a gradient of increasing chemical denaturant it begins to denature and undergoes both a conformational and mobility change. The dsDNA fragment will travel faster than a denatured single-stranded (ss) DNA fragment, since the branched structure of the single-stranded moiety of the molecule becomes entangled in the gel matrix. As the denaturing environment increases, the dsDNA fragment will completely dissociate and mobility of the molecule through the gel is retarded at the denaturant concentration at which the particular low denaturing domains of the DNA strand dissociate. In practice, the electrophoresis is conducted at a constant temperature (around 60° C.) and chemical denaturants are used at concentrations that will result in 100% of the DNA molecules being denatured (i.e., 40% formamide and 7 M urea). This variable denaturing gradient is created using a gradient maker, such that the composition of each DGGE gel gradually changes from 0% denaturant up to 100% denaturant. Of course, gradients containing a reduced range of denaturant (e.g., 35% to 60%) may also be poured for increased separation of DNA.

The principle used in DGGE can also be applied to a second method that uses a temperature gradient instead of a chemical denaturant gradient. This method is known as Temperature Gradient Gel Electrophoresis (TGGE). This method makes use of a temperature gradient to induce the conformational change of dsDNA to ssDNA to separate fragments of equal size with different sequences. As in DGGE, DNA fragments with different nucleotide sequences will become immobile at different positions in the gel. Variations in primer design can be used to advantage in increasing the usefulness of DGGE for characterization and identification of the PCR products. These methods and principles of using primer design variations are described in PCR Technology Principles and Applications, Henry A. Erlich Ed., M. Stockton Press, NY, pages 71 to 88 (1988).

Instrumentation:

When homogenous detection is employed, the level of fluorescence is preferably measured using a laser fluorometer such as, for example, BAX® Q7 machine (DuPont Qualicon, Wilmington, Del.). However, similar detection systems for measuring the level of fluorescence in a sample are included in the invention.

Reagents and Kits:

Any suitable nucleic acid replication composition ("replication composition") in any format can be used. A typical replication composition for PCR amplification may comprise, for example, dATP, dCTP, dGTP, dTTP, target specific primers and a suitable polymerase.

If the replication composition is in liquid form, suitable buffers known in the art may be used (Sambrook, J. et al., supra).

Alternatively, if the replication composition is contained in a tablet form, then typical tabletization reagents may be included such as stabilizers and binding agents. Preferred tabletization technology is set forth in U.S. Pat. Nos. 4,762,857 and 4,678,812, each of which is hereby incorporated by reference in its entirety.

A preferred replication composition of the instant invention comprises (a) the primer pair from Table 1, and (b) thermostable DNA polymerase.

A more preferred replication composition of the present invention comprises (a) the primer pairs and any corresponding probe or blocking oligonucleotide selected from Table 1, wherein each nucleic acid probe or primer-probe complex employed comprises a detectable label; and (b) thermostable DNA polymerase. Preferably the detectable label comprises a reporter capable of emitting a detectable signal and a quencher capable of substantially quenching the reporter and preventing the emission of the detectable signal when the reporter and quencher are in sufficiently close proximity to one another.

A preferred kit of the instant invention comprises any one of the above replication compositions. A preferred tablet of the instant invention comprises any one of the above replication compositions. More preferably, a kit of the instant invention comprises the foregoing preferred tablet.

In some instances, an internal positive control can be included in the reaction. The internal positive control can include control template nucleic acids (e.g. DNA or RNA), control primers, and control nucleic acid probe. The advantages of an internal positive control contained within a PCR reaction have been previously described (U.S. Pat. No. 6,312,930 and PCT Application No. WO 97/11197, each of which is hereby incorporated by reference in its entirety), and include: (i) the control may be amplified using a single primer; (ii) the amount of the control amplification product is independent of any target DNA or RNA contained in the sample; (iii) the control DNA can be tableted with other amplification reagents for ease of use and high degree of reproducibility in both manual and automated test procedures; (iv) the control can be used with homogeneous detection, i.e., without separation of product DNA from reactants; and (v) the internal control has a melting profile that is distinct from other potential amplification products in the reaction and/or a detectable label on the control nucleic acid that is distinct from the detectable label on the nucleic acid probe directed to the target.

Control DNA will be of appropriate size and base composition to permit amplification in a primer-directed amplification reaction. The control template DNA sequence may be obtained from the *E. coli* genome, or from another source, but must be reproducibly amplified under the same conditions that permit the amplification of the target amplification product.

Preferred control sequences include, for example, those found in SV40.

| Primer/Probe | Concentration Range | SEQ ID NO: |
| --- | --- | --- |
| SV4222 | 0.100-0.400 µM | 19 |
| SV4312 | 0.025-0.150 µM | 20 |
| SV40 Scorpion 1 | 0.010-0.100 µM | 21 |

The control reaction is useful to validate the amplification reaction. Amplification of the control DNA occurs within the same reaction tube as the sample that is being tested, and therefore indicates a successful amplification reaction when samples are target negative, i.e. no target amplification product is produced. In order to achieve significant validation of the amplification reaction, a suitable number of copies of the control DNA template must be included in each amplification reaction.

In some instances it may be useful to include an additional negative control replication composition. The negative control replication composition will contain the same reagents as the replication composition but without the polymerase. The primary function of such a control is to monitor spurious background fluorescence in a homogeneous format when the method employs a fluorescent means of detection.

Replication compositions may be modified depending on whether they are designed to be used to amplify target DNA or the control DNA. Replication compositions that will amplify the target DNA (test replication compositions) may include (i) a polymerase (generally thermostable), (ii) a primer pair capable of hybridizing to the target DNA and (iii) necessary buffers for the amplification reaction to proceed. Replication compositions that will amplify the control DNA (positive control, or positive replication composition) may include (i) a polymerase (generally thermostable) (ii) the control DNA; (iii) at least one primer capable of hybridizing to the control DNA; and (iv) necessary buffers for the amplification reaction to proceed. In addition, the replication composition for either target DNA or control DNA amplification can contain a nucleic acid probe, preferably possessing a detectable label.

Nucleic Acid Hybridization Methods

In addition to primer-directed amplification assay methods, nucleic acid hybridization assay methods can be employed in the present invention for detection of *E. coli* O157:H7. The basic components of a nucleic acid hybridization test include a probe, a sample suspected of containing *E. coli* O157:H7, and a specific hybridization method. Typically the probe length can vary from as few as 5 bases to the full length of the *E. coli* diagnostic sequence and will depend upon the specific test to be done. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Probes particularly useful in nucleic acid hybridization methods are any of SEQ ID NOs: 9-13, or sequences derived therefrom.

The sample may or may not contain *E. coli* O157:H7. The sample may take a variety of forms, however will generally be extracted from an animal, environmental or food source suspected of contamination. The DNA may be detected directly but most preferably, the sample nucleic acid must be made available to contact the probe before any hybridization of probe and target molecule can occur. Thus the organism's DNA is preferably free from the cell and placed under the proper conditions before hybridization can occur. Methods of in-solution hybridization necessitate the purification of the DNA in order to be able to obtain hybridization of the sample DNA with the probe. This has meant that utilization of the in-solution method for detection of target sequences in a sample requires that the nucleic acids of the sample must first be purified to eliminate protein, lipids, and other cell components, and then contacted with the probe under hybridization conditions. Methods for the purification of the sample nucleic acid are common and well known in the art (Sambrook et al., supra).

In one preferred embodiment, hybridization assays may be conducted directly on cell lysates, without the need to extract the nucleic acids. This eliminates several steps from the sample-handling process and speeds up the assay. To perform such assays on crude cell lysates, a chaotropic agent is typically added to the cell lysates prepared as described above. The chaotropic agent stabilizes nucleic acids by inhibiting nuclease activity. Furthermore, the chaotropic agent allows sensitive and stringent hybridization of short oligonucleotide probes to DNA at room temperature (Van Ness & Chen, Nucleic Acids Res. 19:5143-51 (1991)). Suitable chaotropic agents include guanidinium chloride, guanidinium thiocyanate, sodium thiocyanate, lithium tetrachloroacetate, sodium perchlorate, rubidium tetrachloroacetate, potassium iodide, and cesium trifluoroacetate, among others. Typically, the chaotropic agent will be present at a final concentration of about 3 M. If desired, one can add formamide to the hybridization mixture, typically 30-50% (v/v).

Alternatively, one can purify the sample nucleic acids prior to probe hybridization. A variety of methods are known to one of skill in the art (e.g., phenol-chloroform extraction, IsoQuick extraction (MicroProbe Corp., Bothell, Wash.), and others). Pre-hybridization purification is particularly useful for standard filter hybridization assays. Furthermore, purification facilitates measures to increase the assay sensitivity by incorporating in vitro RNA amplification methods such as self-sustained sequence replication (see for example Fahy et al., In *PCR Methods and Applications*, Cold Spring Harbor Laboratory: Cold Spring Harbor, N.Y. (1991), pp. 25-33) or reverse transcriptase PCR (Kawasaki, In *PCR Protocols: A Guide to Methods and Applications*, M. A. Innis et al., Eds., (1990), pp. 21-27).

Once the DNA is released, it can be detected by any of a variety of methods. However, the most useful embodiments have at least some characteristics of speed, convenience, sensitivity, and specificity.

Hybridization methods are well known in the art. Typically the probe and sample must be mixed under conditions which will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed.

Various hybridization solutions can be employed. Typically, these comprise from about 20 to 60% volume, preferably 30%, of a polar organic solvent. A common hybridization solution employs about 30-50% v/v formamide, about 0.15 to 1M sodium chloride, about 0.05 to 0.1M buffers, such as sodium citrate, Tris-HCl, PIPES or HEPES (pH range about 6-9), about 0.05 to 0.2% detergent, such as sodium dodecylsulfate, or between 0.5-20 mM EDTA, FICOLL (Pharmacia Inc.) (about 300-500 kilodaltons), polyvinylpyrrolidone (about 250-500 kdal), and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol glycine. Other additives may also be included, such as volume exclusion agents which include a variety of polar water-soluble or swellable agents (e.g., polyethylene glycol), anionic polymers (e.g., polyacrylate or polymethylacrylate), and anionic saccharidic polymers (e.g., dextran sulfate).

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the DNA sequence.

The sandwich assay may be encompassed in an assay kit. This kit would include a first component for the collection of samples suspected of contamination and buffers for the disbursement and lysis of the sample. A second component would include media in either dry or liquid form for the hybridization of target and probe polynucleotides, as well as for the removal of undesirable and nonduplexed forms by washing. A third component includes a solid support (dipstick) upon which is fixed (or to which is conjugated) unlabeled nucleic acid probe(s) that is (are) complementary to one or more of the sequences disclosed herein. A fourth component would contain labeled probe that is complementary to a second and different region of the same DNA strand to which the immobilized, unlabeled nucleic acid probe of the third component is hybridized.

In a preferred embodiment, polynucleotide sequences disclosed herein or derivations thereof may be used as 3' blocked detection probes in either a homogeneous or heterogeneous assay format. For example, a probe generated from these sequences may be 3' blocked or non-participatory and will not be extended by, or participate in, a nucleic acid amplification reaction. Additionally, the probe incorporates a label that can serve as a reactive ligand that acts as a point of attachment for the immobilization of the probe/analyte hybrid or as a reporter to produce detectable signal. Accordingly, genomic or cDNA isolated from a sample suspected of *E. coli* contamination is amplified by standard primer-directed amplification protocols in the presence of an excess of the 3' blocked detection probe to produce amplification products. Because the probe is 3' blocked, it does not participate or interfere with the amplification of the target. After the final amplification cycle, the detection probe anneals to the relevant portion of the amplified DNA and the annealed complex is then captured on a support through the reactive ligand.

In some instances it is desirable to incorporate a ligand labeled dNTP, with the label probe in the replication composition to facilitate immobilization of the PCR reaction product on a support and then detection of the immobilized product by means of the labeled probe reagent. For example a biotin, digoxigenin, or digoxin labeled dNTP could be added to PCR reaction composition. The biotin, digoxigenin, or digoxin incorporated in the PCR product could then be immobilized respectively on to a strepavidin, antidixogin or antidigoxigenin antibody support. The immobilized PCR product could then be detected by the presence of the probe label.

EXAMPLES

The present invention is further defined in the following Examples. It should be understood that these Examples, while indicating preferred embodiments of the invention, are given by way of illustration only.

General Methods and Materials Used in the Examples

Materials and methods suitable for the maintenance and growth of bacterial cultures are well known in the art. Techniques suitable for use in the following Examples may be found in Manual of Methods for Genus Bacteriology (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994) or Thomas D. Brock in Biotechnology: A Textbook of Industrial Microbiology, Second Edition (1989) Sinauer Associates, Inc., Sunderland, Mass. or Bacteriological Analytical Manual. 6th Edition, Association of Official Analytical Chemists, Arlington, Va. (1984).

Primers and probes (SEQ ID NOs: 1, 2, 9, 10, 14, and 15) were prepared by Biosearch Technologies, Inc., 81 Digital Drive, Novato, Calif. 94949 USA.

All PCR reactions were carried out using a standard BAX® System (DuPont Qualicon, Wilmington, Del.).

The meaning of abbreviations is as follows: "h" means hour(s), "min" means minute(s), "sec" means second(s), "d" means day(s), "ml" means milliliter(s), "μl" means microliter(s), "cfu" means colony forming unit(s), M means molar, μM means micromolar, nM means nanomolar.

Example 1

Determination of Inclusivity/Exclusivity of the Individual Targets Via Scorpion® Assay Samples of organisms were analyzed to establish inclusivity and exclusivity of Scorpion® probes of the present invention. Pure cultures grown overnight achieved cell densities of approximately $1\times10^9$ cfu/ml. For inclusivity, independent, bona fide O157:H7 isolates were used; for exclusivity, closely related non-target organisms to ensure that the assay would discriminate the target organisms from other non-target organisms.

DNA Lysate Preparation for Inclusivity and Exclusivity

Material tested was overnight growth pure cultures of the target and non-target organisms grown at 37° C. in BHI media. For exclusivity, non-diluted overnight cultures were tested. For inclusivity, overnight cultures were diluted approximately 1:10,000 into TSB. 20 μl of the material to be tested was added to 200 μl of BAX® lysis reagent (DuPont Qualicon, Wilmington, Del.). The mixture was incubated at 37° C. for 20 minutes, then further incubated at 95° C. for 10 minutes, and finally cooled to 5° C.

PCR Conditions 5-30 μl of the DNA lysate as prepared above was used to hydrate lyophylized PCR reaction components to achieve a DNA lysate/PCR reaction component mixture containing the primers and Scorpions® listed in Table 2.

TABLE 2

| Primers | SEQ ID NO | Per reaction | Dye |
|---|---|---|---|
| O157H7T3-89-24 (100 μM) | 1 | 200-300 nM | |
| O157H7T3-rc218-23 (100 μM) | 2 | 200-300 nM | |
| Probe 1 - O157H7T3-89 (100 μM) | 9-18 carbon spacer-1 | 20-60 nM | Calfluor Gold 540 |
| Quencher - O157H7T3#1 (100 μM) | 14 | 60-180 nM | BHQ-1 ™ |
| Probe 2 - O157H7T3-rc218 (100 μM) | 10-18 carbon spacer-2 | 20-60 nM | Calfluor Gold 540 |
| Quencher - O157H7T3#2 (100 μM) | 15 | 60-180 nM | BHQ-1 ™ |

This DNA lysate/PCR reaction component mixture was added to a PCR reaction mixture. The reagents that were used in the PCR amplification reaction were custom made lyophilized reagent tablets containing GoTaq DNA Polymerase (Promega, Madison, Wis., USA), deoxynucleotides (Roche Diagnostics, Indianapolis, Ind.), BSA and surfactamps (Sigma-Aldrich, St. Louis, Mo.) In addition PCR buffer (DuPont Qualicon, Wilmington, Del.) was used.

Amplification and testing was performed on the BAX® Q7 machine (DuPont Qualicon, Wilmington, Del.). The thermal cycling conditions were: 2 minutes at 94° C., followed by 43 cycles of 94° C. for 10 seconds and 63° C. for 40 seconds, with the fluorescent signal captured during the 63° C. step at each cycle.

Results

As can be seen in Tables 3-4, below, using individual Scorpion® probes, the method of the present invention was able to correctly detect all of the O157:H7 isolates and none of the non-O157:H7 isolates or real-world enrichments not containing O157:H7.

TABLE 3

O157:H7 Inclusivity

| Isolate Number | Isolate Source | Serovar | BAX ® System Result: O157:H7 |
|---|---|---|---|
| 640 | ATCC | O157:H7 | Positive |
| 641 | ATCC; Human feces | O157:H7 | Positive |
| 642 | ATCC | O157:H7 | Positive |
| 914 | ATCC | O157:H7 | Positive |
| 915 | ATCC | O157:H7 | Positive |
| 916 | ATCC; Human feces | O157:H7 | Positive |
| 935 | | O157:H7 | Positive |
| 1449 | | O157:H7 | Positive |
| 1451 | | O157:H7 | Positive |
| 1453 | | O157:H7 | Positive |
| 1455 | Human bloody diarrhea | O157:H7 | Positive |
| 1458 | | O157:H7 | Positive |
| 1459 | | O157:H7 | Positive |
| 1973 | | O157:H7 | Positive |
| 1976 | | O157:H7 | Positive |
| 1977 | | O157:H7 | Positive |
| 1979 | Hamburger | O157:H7 | Positive |
| 1982 | Cow's faeces | O157:H7 | Positive |
| 1983 | Beef | O157:H7 | Positive |
| 1986 | Pork | O157:H7 | Positive |
| 1987 | Veal | O157:H7 | Positive |
| 1988 | Hamburger | O157:H7 | Positive |
| 1989 | | O157:H7 | Positive |
| 1990 | | O157:H7 | Positive |
| 1991 | | O157:H7 | Positive |
| 5893 | | O157:H7 | Positive |
| 5895 | | O157:H7 | Positive |
| 6972 | | O157:H7 | Positive |
| 7101 | | O157:H7 | Positive |
| 8296 | | O157:H7 | Positive |
| 8297 | | O157:H7 | Positive |
| 8299 | | O157:H7 | Positive |
| 8301 | | O157:H7 NM | Positive |
| 8856 | Stool of patient with hemolyti | O157:H7 | Positive |
| 8857 | Human feces, CA | O157:H7 | Positive |
| 8858 | Human stool from outbreak | O157:H7 | Positive |
| 8860 | | O157:H7 | Positive |
| 8865 | | O157:H7 | Positive |
| 8866 | | O157:H7 | Positive |
| 8868 | Patient in 1986; epidemiologic | O157:H7 | Positive |
| 8872 | | O157:H7 | Positive |
| 8873 | Patient in 1993 outbreak | O157:H7 | Positive |
| 9048 | | O157:H7 | Positive |
| 9048 | | O157:H7 | Positive |
| 9712 | | O157:H7 | Positive |
| 10133 | Jun. 13, 1994 | O157:H7 | Positive |
| 10901 | | O157:H7 | Positive |
| 10909 | | O157:H7 | Positive |
| 10910 | | O157:H7 | Positive |
| 10913 | | O157:H7 | Positive |
| 10922 | | O157:H7 | Positive |
| 12787 | PSU ECRC | O157:H7 | Positive |
| 12788 | | O157:H7 | Positive |
| 12791 | | O157:H7 | Positive |
| 12793 | | O157:H7 | Positive |
| 12797 | | O157:H7 | Positive |
| 12806 | | O157:H7 | Positive |
| 12807 | | O157:H7 | Positive |
| 12814 | | O157:H7 | Positive |
| 12818 | | O157:H7 | Positive |
| 12825 | | O157:H7 | Positive |
| 12828 | | O157:H7 | Positive |
| 12836 | | O157:H7 | Positive |
| 12844 | | O157:H7 | Positive |
| 12857 | | O157:H7 | Positive |
| 12862 | | O157:H7 | Positive |
| 12864 | PSU ECRC | O157:H7 | Positive |
| 12865 | PSU ECRC | O157:H7 | Positive |
| 12871 | | O157:H7 | Positive |
| 12877 | | O157:H7 | Positive |
| 12882 | | O157:H7 | Positive |
| 12884 | | O157:H7 | Positive |
| 12905 | 700728 | O157:H7 | Positive |
| 12905 | | O157:H7 | Positive |
| 13038 | ground beef | O157:H7 | Positive |
| 13040 | ATCC; Human feces | O157:H7 | Positive |
| 13040 | ATCC | O157:H7 | Positive |
| 13054 | ground beef | O157:H7 | Positive |
| 13055 | ground beef | O157:H7 | Positive |
| 13072 | | O157:H7 | Positive |
| 13077 | beef trim | O157:H7 | Positive |
| 13078 | | O157:H7 | Positive |
| 13085 | | O157:H7 | Positive |
| 13175 | | O157:H7 | Positive |
| 13176 | beef isolate | O157:H7 | Positive |
| 13182 | | O157:H7 | Positive |
| 13189 | | O157:H7 | Positive |
| 13197 | | O157:H7 | Positive |
| 13241 | | O157:H7 | Positive |
| 13262 | | O157:H7 | Positive |
| 13291 | | O157:H7 | Positive |
| 13405 | | O157:H7 | Positive |
| 13406 | Beef | O157:H7 | Positive |
| 13407 | | O157:H7 | Positive |
| 13482 | | O157:H7 | Positive |
| 13483 | | O157:H7 | Positive |

TABLE 4

Exclusivity

| Isolate Number | Species | Serovar | BAX ® System Result: O157:H7 |
|---|---|---|---|
| 1718 | E. coli | O128:H2 | Negative |
| 1721 | E. coli | O114:H32 | Negative |
| 1730 | E. coli | O86:H25 | Negative |
| 1732 | E. coli | O143:HNM | Negative |
| 1762 | E. coli | O164:HNM | Negative |
| 1769 | E. coli | O139:H1 | Negative |
| 1770 | E. coli | O115:H18 | Negative |
| 1803 | E. coli | O25:H(−) | Negative |
| 1814 | E. coli | O6:H(−) | Negative |
| 1821 | E. coli | O55:H(−) | Negative |
| 1827 | E. coli | O20:HNM | Negative |
| 1835 | E. coli | O127:H(−) | Negative |
| 1836 | E. coli | O125:H(−) | Negative |
| 1842 | E. coli | O78:HNM | Negative |
| 1861 | E. coli | O126:H(−) | Negative |
| 1889 | E. coli | O152:H10 | Negative |
| 1915 | E. coli | O28:H(−) | Negative |
| 2432 | E. coli | O165:H(−) | Negative |
| 2434 | E. coli | O1:H7 | Negative |
| 2438 | E. coli | O118:HNM | Negative |
| 2441 | E. coli | O117:H4 | Negative |
| 2443 | E. coli | O157:H19 | Negative |
| 2445 | E. coli | O113:H21 | Negative |

TABLE 4-continued

| Exclusivity | | | |
|---|---|---|---|
| Isolate Number | Species | Serovar | BAX ® System Result: O157:H7 |
| 2480 | E. coli | O2 | Negative |
| 2485 | E. coli | O157:H19 | Negative |
| 3124 | E. coli | O2 | Negative |
| 3130 | E. coli | O8 | Negative |
| 5884 | E. coli | O91:H− | Negative |
| 12887 | E. coli | O157:H2 | Negative |
| 12889 | E. coli | O157:H4 | Negative |
| 12890 | E. coli | O157:H11 | Negative |
| 12891 | E. coli | O157:H12 | Negative |
| 12892 | E. coli | O157:H29 | Negative |
| 12893 | E. coli | O157:H32 | Negative |
| 12894 | E. coli | O157:H43 | Negative |
| 12896 | E. coli | O157:H44 | Negative |
| 12897 | E. coli | O157:H54 | Negative |
| 13415 | E. coli | O165:H25 | Negative |
| 13416 | E. coli | O85:NM TB334 | Negative |
| 13417 | E. coli | O4:HNM 85-3377 | Negative |
| 13418 | E. coli | O14:HNM 95-3209 | Negative |
| 13419 | E. coli | O22:H5 95-3322 | Negative |
| 13420 | E. coli | O28ac:H25 96-3286 | Negative |
| 13421 | E. coli | O38:H21 96-3307 | Negative |
| 13422 | E. coli | O48:H21 95-3022 | Negative |
| 13423 | E. coli | O79:H7 96-F368851 | Negative |
| 13424 | E. coli | O83:H1 90-3119 | Negative |
| 13425 | E. coli | O88:H25 96-9840 | Negative |
| 13426 | E. coli | O93R26:H19 96-3007 | Negative |
| 13427 | E. coli | O104:H21 94-3024 | Negative |
| 13428 | E. coli | O117:H7 97-3039 | Negative |
| 13429 | E. coli | O119:HNM 96-3032 | Negative |
| 13430 | E. coli | O125ac:HNM 86-3153 | Negative |
| 13431 | E. coli | O126:H27 89-3506 | Negative |
| 13432 | E. coli | O128:H45-96-3305 | Negative |
| 13433 | E. coli | O137:H41 88-3493 | Negative |
| 13434 | E. coli | O146:H21 90-3158 | Negative |
| 13435 | E. coli | O165:H25 88-3001 | Negative |
| 13436 | E. coli | OX1H21 89-3156 | Negative |
| 13437 | E. coli | O113:H21 O4-1450 | Negative |
| 13438 | E. coli | O165:H25 00-4540 | Negative |
| 13439 | E. coli | O5:NM 03-2682 | Negative |
| 13440 | E. coli | O55:H7 05-0376 | Negative |
| 13441 | E. coli | O91:H21 85-489 | Negative |
| 13442 | E. coli | O2:H25 SJ4 | Negative |
| 13443 | E. coli | O2:H27 SJ5 | Negative |
| 13444 | E. coli | O2:H27 SJ6 | Negative |
| 13445 | E. coli | O128:NM SJ19 | Negative |
| 13446 | E. coli | O128:H2 SJ20 | Negative |
| 13447 | E. coli | O63:H6 SJ88 | Negative |
| 13448 | E. coli | O63:NM SJ87 | Negative |
| 13449 | E. coli | O63:H49 F6069 | Negative |
| 13450 | E. coli | O113:H21 SJ29 | Negative |
| 13451 | E. coli | O113:H21 SJ30 | Negative |
| 13452 | E. coli | O113:H21 8J31 | Negative |
| 13453 | E. coli | O91:H21 SJ32 | Negative |
| 13454 | E. coli | O4:HNM | Negative |
| 13456 | E. coli | O2:H27 E18 | Negative |
| 13457 | E. coli | O2:H27 E19 | Negative |
| 13458 | E. coli | O174:H8 AA1 | Negative |
| 13459 | E. coli | O55:H7 BB2 | Negative |
| 13460 | E. coli | O128ac:[H2] CC3 | Negative |
| 13461 | E. coli | O177:[H25] DD4 | Negative |
| 13462 | E. coli | O111:[H8] EE5 | Negative |
| 13463 | E. coli | O113:H4 FF6 | Negative |
| 13464 | E. coli | O103:H2 GG7 | Negative |
| 13465 | E. coli | O26:H11 HH8 | Negative |
| 13466 | E. coli | O41:H26 II9 | Negative |
| 13468 | E. coli | O138 TW05622 | Negative |
| 13469 | E. coli | O91:H21 B2F1 | Negative |
| 13470 | E. coli | O83:H6 CB9764 | Negative |
| 13471 | E. coli | O63:H6 CB10019 | Negative |
| 13472 | E. coli | O8:H− K102-1 | Negative |
| 13473 | E. coli | O2:H44 K2-43 | Negative |
| 13474 | E. coli | VN96 | Negative |
| 13475 | E. coli | VN81 | Negative |
| 13476 | E. coli | VN65 | Negative |
| 13479 | E. coli | O73 | Negative |

What is claimed is:

1. A method for detecting the presence of *E. coli* O157:H7 in a sample, said sample comprising nucleic acids, said method comprising:
   (a) providing a reaction mixture comprising a primer pair selected from the group consisting of primer pair SEQ ID NO:1 and SEQ ID NO:2, primer pair SEQ ID NO:3 and SEQ ID NO:4, primer pair SEQ ID NO:5 and SEQ ID NO:6, primer pair SEQ ID NO:7 and SEQ ID NO:8, and a combination thereof;
   (b) performing PCR amplification of said nucleic acids of said sample using the reaction mixture of step (a); and
   (c) detecting the amplification of step (b), whereby a positive detection of amplification indicates the presence of *E. coli* O157:H7 in the sample.

2. The method of claim 1, wherein said reaction mixture further comprises a nucleic acid probe.

3. The method of claim 2, wherein said nucleic acid probe comprises SEQ ID NO:9, SEQ ID NO:10, SEQ ID NO:11, SEQ ID NO:12, SEQ ID NO:13, or a combination thereof.

4. The method of claim 3, wherein said probe further comprises a detectable label.

5. The method of claim 4, wherein said reaction mixture further comprises a blocking oligonucleotide capable of quenching said detectable label of said probe, said blocking oligonucleotide comprising SEQ ID NO:14, SEQ ID NO:15, SEQ ID NO:16, SEQ ID NO:17, SEQ ID NO:18, or a combination thereof.

6. The method of claim 5, wherein said reaction mixture comprises primer pair SEQ ID NO:1 and SEQ ID NO:2, probes SEQ ID NO:9 and SEQ ID NO:10, and blocking oligonucleotides SEQ ID NO:14 and SEQ ID NO:15.

7. The method of claim 1, wherein the sample comprises a food sample or a water sample.

8. An isolated polynucleotide comprising a nucleotide sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, and SEQ ID NO:18, wherein said polynucleotide comprises a primer region and a probe region, and wherein said polynucleotide further comprises a non-amplifiable linker joining said primer region to said probe region.

9. The isolated polynucleotide of claim 8, wherein said non-amplifiable linker is an 18-carbon non-amplifiable linker, and wherein said polynucleotide further comprises a detectable label.

10. A replication composition for use in performance of PCR, comprising:
  (a) a primer pair selected from the group consisting of primer pair SEQ ID NO:1 and SEQ ID NO:2, primer pair SEQ ID NO:3 and SEQ ID NO:4, primer pair SEQ ID NO:5 and SEQ ID NO:6, primer pair SEQ ID NO:7 and SEQ ID NO:8, and a combination thereof; and
  (b) a nucleic acid probe comprising a detectable label.

11. The replication composition of claim 10 further comprising a blocking oligonucleotide selected from the group consisting of SEQ ID NO:14, SEQ ID NO:15, SEQ ID NO:16, SEQ ID NO:17, SEQ ID NO:18, and a combination thereof.

12. The replication composition of claim 11, wherein said nucleic acid probe comprises SEQ ID NO:9, SEQ ID NO:10, SEQ ID NO:11, SEQ ID NO:12, SEQ ID NO:13, or a combination thereof.

13. The replication composition of claim 12, wherein said replication composition comprises primer pair SEQ ID NO:1 and SEQ ID NO:2, probes SEQ ID NO:9 and SEQ ID NO:10, and blocking oligonucleotides SEQ ID NO:14 and SEQ ID NO:15.

14. A kit for detection of *E. coli* O157:H7 in a sample, comprising the replication composition of claim 10.

15. A tablet comprising the replication composition of claim 10.

* * * * *

SEQUENCE LISTING

<160> NUMBER OF SEQ ID NOS: 21

<210> SEQ ID NO 1
<211> LENGTH: 24
<212> TYPE: DNA
<213> ORGANISM: Artificial Sequence
<220> FEATURE:
<223> OTHER INFORMATION: Primer

<400> SEQUENCE: 1
ttgttgaagg aaaagtgctg cgtc                                     24

<210> SEQ ID NO 2
<211> LENGTH: 23
<212> TYPE: DNA
<213> ORGANISM: Artificial Sequence
<220> FEATURE:
<223> OTHER INFORMATION: Primer

<400> SEQUENCE: 2
ccagtcatcg tctgacaacg ggt                                      23

<210> SEQ ID NO 3
<211> LENGTH: 22
<212> TYPE: DNA
<213> ORGANISM: Artificial Sequence

```
<220> FEATURE:
<223> OTHER INFORMATION: Primer

<400> SEQUENCE: 3
taccgaagag gtgatgctgg ac                                              22

<210> SEQ ID NO 4
<211> LENGTH: 22
<212> TYPE: DNA
<213> ORGANISM: Artificial Sequence
<220> FEATURE:
<223> OTHER INFORMATION: Primer

<400> SEQUENCE: 4
ccttcacctt agccagtcgc tg                                              22

<210> SEQ ID NO 5
<211> LENGTH: 22
<212> TYPE: DNA
<213> ORGANISM: Artificial Sequence
<220> FEATURE:
<223> OTHER INFORMATION: Primer

<400> SEQUENCE: 5
aaattaccgg aaaaacgccg gt                                              22

<210> SEQ ID NO 6
<211> LENGTH: 22
<212> TYPE: DNA
<213> ORGANISM: Artificial Sequence
<220> FEATURE:
<223> OTHER INFORMATION: Primer

<400> SEQUENCE: 6
gtcatctcgc ccggcgtcag at                                              22

<210> SEQ ID NO 7
<211> LENGTH: 18
<212> TYPE: DNA
<213> ORGANISM: Artificial Sequence
<220> FEATURE:
<223> OTHER INFORMATION: Primer

<400> SEQUENCE: 7
tggcggccta tgtctccc                                                   18

<210> SEQ ID NO 8
<211> LENGTH: 26
<212> TYPE: DNA
<213> ORGANISM: Artificial Sequence
<220> FEATURE:
<223> OTHER INFORMATION: Primer

<400> SEQUENCE: 8
gttatcatcg taggattctg ccgtca                                          26

<210> SEQ ID NO 9
<211> LENGTH: 26
<212> TYPE: DNA
<213> ORGANISM: Artificial Sequence
<220> FEATURE:
<223> OTHER INFORMATION: Probe

<400> SEQUENCE: 9
cggacgtaac acgcgggttt caccac                                          26
```

<210> SEQ ID NO 10
<211> LENGTH: 28
<212> TYPE: DNA
<213> ORGANISM: Artificial Sequence
<220> FEATURE:
<223> OTHER INFORMATION: Probe

<400> SEQUENCE: 10
tgggtttata acggtcaggg tgacgcct                                    28

<210> SEQ ID NO 11
<211> LENGTH: 28
<212> TYPE: DNA
<213> ORGANISM: Artificial Sequence
<220> FEATURE:
<223> OTHER INFORMATION: Probe

<400> SEQUENCE: 11
tgcaaacccg ttgtcagacg atgactgg                                    28

<210> SEQ ID NO 12
<211> LENGTH: 28
<212> TYPE: DNA
<213> ORGANISM: Artificial Sequence
<220> FEATURE:
<223> OTHER INFORMATION: Probe

<400> SEQUENCE: 12
gactggcagc gactggctaa ggtgaagg                                    28

<210> SEQ ID NO 13
<211> LENGTH: 28
<212> TYPE: DNA
<213> ORGANISM: Artificial Sequence
<220> FEATURE:
<223> OTHER INFORMATION: Probe

<400> SEQUENCE: 13
tgacgcagca cttttccttc aacaaccg                                    28

<210> SEQ ID NO 14
<211> LENGTH: 26
<212> TYPE: DNA
<213> ORGANISM: Artificial Sequence
<220> FEATURE:
<223> OTHER INFORMATION: Quencher

<400> SEQUENCE: 14
gtggtgaaac ccgcgtgtta cgtccg                                      26

<210> SEQ ID NO 15
<211> LENGTH: 28
<212> TYPE: DNA
<213> ORGANISM: Artificial Sequence
<220> FEATURE:
<223> OTHER INFORMATION: Quencher

<400> SEQUENCE: 15
aggcgtcacc ctgaccgtta taaaccca                                    28

<210> SEQ ID NO 16
<211> LENGTH: 23
<212> TYPE: DNA
<213> ORGANISM: Artificial Sequence
<220> FEATURE:
<223> OTHER INFORMATION: Quencher

```
<400> SEQUENCE: 16
catcgtctga caacgggttt gca                                        23

<210> SEQ ID NO 17
<211> LENGTH: 22
<212> TYPE: DNA
<213> ORGANISM: Artificial Sequence
<220> FEATURE:
<223> OTHER INFORMATION: Quencher

<400> SEQUENCE: 17
accttagcag tcgctgccag tc                                         22

<210> SEQ ID NO 18
<211> LENGTH: 23
<212> TYPE: DNA
<213> ORGANISM: Artificial Sequence
<220> FEATURE:
<223> OTHER INFORMATION: Quencher

<400> SEQUENCE: 18
gttgaaggaa aagtgctgcg tca                                        23

<210> SEQ ID NO 19
<211> LENGTH: 29
<212> TYPE: DNA
<213> ORGANISM: Artificial Sequence
<220> FEATURE:
<223> OTHER INFORMATION: Primer

<400> SEQUENCE: 19
aatagcagac actctatgcc tgtgtggag                                  29

<210> SEQ ID NO 20
<211> LENGTH: 33
<212> TYPE: DNA
<213> ORGANISM: Artificial Sequence
<220> FEATURE:
<223> OTHER INFORMATION: Primer

<400> SEQUENCE: 20
ctttgctatt tacaccacaa aggaaaaagc tgc                             33

<210> SEQ ID NO 21
<211> LENGTH: 78
<212> TYPE: DNA
<213> ORGANISM: Artificial Sequence
<220> FEATURE:
<223> OTHER INFORMATION: Probe

<400> SEQUENCE: 21
aacccaccca gaatattttt ccataatttt cttgtatagc agtgggtggg tttatttaca    60
ccacaaagga aaagctg                                               78
```